(12) United States Patent
Chute et al.

(10) Patent No.: US 6,642,049 B1
(45) Date of Patent: Nov. 4, 2003

(54) HUMAN BRAIN ENDOTHELIAL CELLS AND GROWTH MEDIUM AND METHOD FOR EXPANSION OF PRIMITIVE CD34+CD38- BONE MARROW STEM CELLS

(75) Inventors: John P. Chute, San Francisco, CA (US); Abha A. Saini, Collegeville, PA (US); Dennis J. Chute, Los Angeles, CA (US); Thomas A. Davis, Newton, PA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/452,855

(22) Filed: Dec. 3, 1999

Related U.S. Application Data

(60) Provisional application No. 60/112,042, filed on Dec. 4, 1998.

(51) Int. Cl.$^7$ ............... C12N 5/00; C12N 5/08
(52) U.S. Cl. .............. 435/373; 435/368; 435/384; 435/385
(58) Field of Search ................ 435/373, 384, 435/385, 368

(56) References Cited

U.S. PATENT DOCUMENTS

| | | | |
|---|---|---|---|
| 5,599,703 A | * | 2/1997 | Davis et al. |
| 5,965,437 A | * | 10/1999 | Scadden |
| 5,969,105 A | * | 10/1999 | Feng et al. |
| 6,228,117 B1 | * | 5/2001 | De Bruijn et al. |

OTHER PUBLICATIONS

"tissue culture" Encyclopædia Britannica <http://www.search.eb.com/eb/article?eu=74530> [Accessed Sep. 4, 2002].*

* cited by examiner

*Primary Examiner*—James Ketter
*Assistant Examiner*—Bronwen M. Loeb
(74) *Attorney, Agent, or Firm*—Joseph K. Hemby, Jr.; A. David Spevack

(57) ABSTRACT

A novel co-culture system using human brain endothelial cells (HUBEC) which promotes the expansion of human $CD34^+CD38^-$ cells consistent with the PMVEC system is disclosed. HUBEC were isolated from cadaveric donors, passed in primary culture, cloned and found to be Von Willebrand Factor positive. Cultivation of purified bone marrow $CD34^+$ cells on HUBEC monolayers supplemented with GM-CSF+IL-3+IL-6+SCF+flt-3 ligand caused a 14.5-fold increase in total cells, an 6.6-fold increase in $CD34^+$ cells, and, most remarkably, a 440-fold increase in $CD34^+CD38^-$ cells after 7 days. Further, CFU-GM production increased 15.1-fold, BFU-E increased 8-fold, and CFU-Mix increased 5.2-fold. Optimal generation was dependent upon the continued presence of exogenous supplied cytokines. Moreover, we found that non-brain human endothelial cells isolated from the same donors supported neither the expansion nor the maintenance of human $CD34^+CD38^-$ cells.

15 Claims, 6 Drawing Sheets

HUMAN BRAIN ENDOTHELIAL CELLS AND GROWTH MEDIUM AND METHOD FOR EXPANSION OF PRIMITIVE CD34+CD38− BONE MARROW STEM CELLS

RELATED APPLICATION

Benefit of U.S. Provisional Application No. 60/112,042 filed Dec. 4, 1998, which is incorporated herein by reference, is claimed.

BACKGROUND OF THE INVENTION

1. Field of the Invention

This invention relates to a growth medium derived from human brain endothelial cells (HUBEC) and the methods of utilizing said growth medium to expand bone marrow stem cells.

2. Description of the Prior Art

The development of an ex-vivo system which supports the proliferation and expansion of the most primitive hematopoietic stem cells (HSC) would have direct application to the fields of gene therapy and stem cell transplantation. Identification and characterization of the optimal culture conditions for the expansion of long-term repopulating cells is a requirement for gene therapy protocols and other stem cell-based therapies.

Various cytokine combinations and liquid culture methods have been shown to support the proliferation of $CD34^+$ HPC in vitro, but the most primitive $CD34^+CD38^-$ cells are frequently lost due to differentiation and cell death [1–6]. In contrast, other investigations have demonstrated that when human HPC are co-cultured in contact with autologous, allogeneic, and xenogeneic bone marrow stroma, a small percentage of long term culture initiating cells (LTC-IC) can be maintained over several weeks [7–9]. Similarly, others have reported the expansion and differentiation of LTC-IC and CFC in stroma-free liquid suspension cultures using exogenous cytokines plus conditioned medium from bone marrow stromal cultures [10–12]. Most recently, it was reported that human cord blood $CD34^+$ cells could be maintained in stroma-free liquid cultures in the presence of flt-3 ligand, megakaryocyte growth and development factor (MGDF), SCF, and IL-6 for up to 10 weeks without losing their ability to repopulate NOD/SCID mice [13].

Vascular endothelium, reticuloendothelial elements, and hematopoietic cells of all types have been postulated to arise from hemangioblasts, a primitive embryonic cell of mesodermal origin [14,15]. During the earliest stages (day 7–8 postcoitum) of mammalian embryonic hematopoiesis, primitive hematopoietic stem cells are found encased in blood islands which derive from aggregates of mesodermal cells which have colonized the embryonic yolk sac [16]. Bone marrow, umbilical vein, and murine yolk sacendothelial cell lines have been shown to elaborate a number of growth factors that regulate early hematopoiesis [17–20]. In addition, the long term proliferation and differentiation of myeloid, erythroid, and megakaryocytic progenitor cells has been demonstrated in vitro using microvascular endothelial cells derived from adult bone marrow and embryonic yolk sac [18,19]. However, the fate of the most primitive $CD34^+CD38^-$ progenitor cells following co-culture with endothelial cell monolayers has not been well demonstrated. Previously, we reported that a primary porcine microvascular endothelial cell line (PMVEC) supports a rapid and robust expansion of human hematopoietic cells exhibiting the primitive $CD34^+CD38^-$ phenotype [21,22]. Unlike other reported co-culture systems, we have demonstrated that $CD34^+CD38^-$ cells expanded on brain endothelium retain the ability to successfully engraft in vivo in both a SCID-Hu bone model [23] and in lethally irradiated baboons [24].

Human brain vascular endothelial cells are similar to other sources of endothelial cells in that they develop cobblestone morphology in-vitro [25], and they express cell adhesion.molecules (selectins, integrins) which mediate the "rolling", adherence, and trafficking of leukocytes [26,27]. Based upon our observations of the hematopoietic capacity of PMVEC and recognizing the limitations of applying a porcine endothelial cell line in human clinical studies, we isolated. primary human brain endothelial cells (HUBEC) and evaluated their capacity to support the ex-vivo expansion of human $CD34^+CD38^-$ cells. Our results indicate that human brain endothelial cells support a unique expansion and apparent self-renewal of the most primitive $CD34^+CD38^-$ HPC at a level comparable to our observations with porcine endothelial cells. Further investigations evaluating the in vivo repopulating potential of HUBEC-expanded HPC will be important in implementing future gene therapy, cord blood expansion, and stem cell transplant protocols.

SUMMARY OF THE INVENTION

Accordingly, an object of this invention is a growth medium based on human brain endothelial cells (HUBEC).

Another object of the invention is the growth factor contained within the medium that is elaborated by the HUBEC and promotes the expansion of primitive CD34+ CD38− bone marrow stem cells.

A further object of this invention is a method for expanding the population of primitive CD34+ CD38− bone marrow stem cells.

Yet another object of this invention is the treated, concentrated product of the growth medium containing the growth factor.

An additional object of the invention is a growth medium that can be used for GMP production of expanded cells.

These and additional objects of the invention are accomplished by human brain endothelial cells (HUBEC) that can serve as a uniquely supportive hematopoietic microenvironmnent.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures are diagrammatic and no attempt is made to indicate actual scales or precise ratios. Proportional relationships are shown as approximations.

Figure 1A:
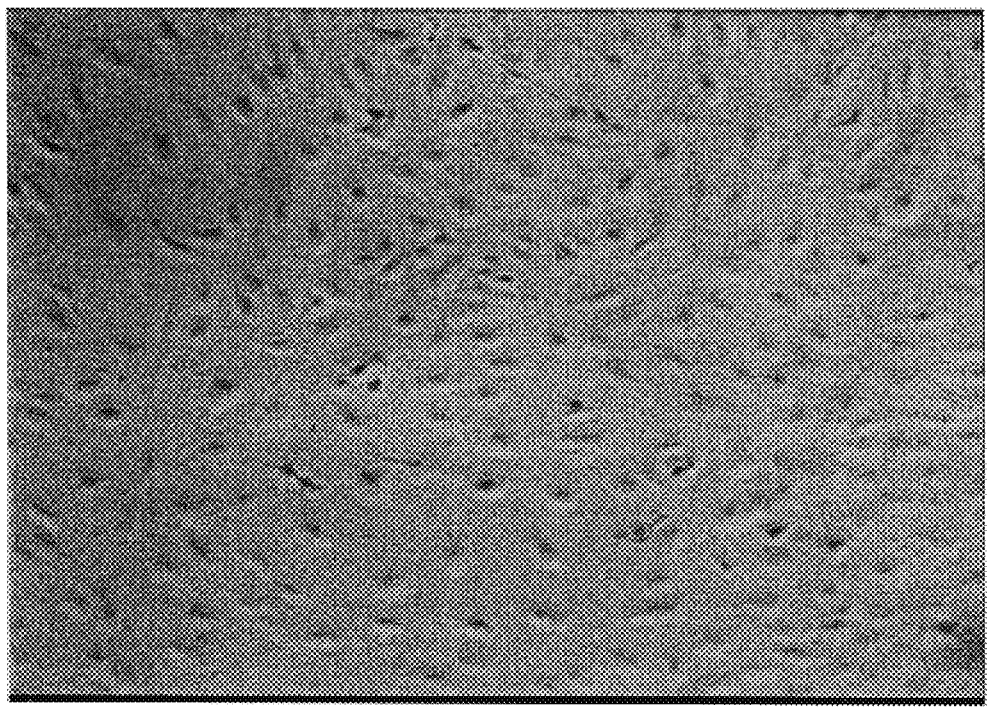
FIGS. 1A and 1B. Phenotype of HUBEC in primary culture. A. typical cobblestone morphology of HUBEC (passage 10) from a confluent (40×magnification). B. Von Willebrand expression by cultured HUBEC (passage 10) was analyzed by flow cytometeric analysis. Isotype-matched control Ab is indicated by a heavy solid line while FITC-conjugated anti-human Von Willebrand staining is depicted by the dotted line.

A) Dispersed colony of hematopoietic cells adherent to HUBEC monolayers after vigorous washing (40×).

B) B) Adherent colony of hematopoietic cells on HUBEC monolayer stained with Wrights' Geimsa stain (100×).

FIGS. 3A, 3B, 3C and 3D. Flow cytometric analysis of expanded CD34+ bone marrow cells following HUBEC co-culture vs. stroma-free liquid culture vs. Human non-brain endothelial cell co-culture. Purified human CD34+ cells were seeded on HUBEC monolayers or in stroma-free liquid culture or in co-culture with non-brain endothelial cell monolayers in the presence of GMCSF+IL-3+IL-6+SCF+flt-3 ligand and cultured for 7 days. The phenotype of purified bone marrow CD34+ cells at day 0 (input) is shown in (A). After 7 days, non-adherent hematopoietic cells were harvested from the HUBEC co-cultures (B), the liquid suspension cultures (C), and the non-brain endothelial cell co-cultures (D), and stained with FITC-conjugated CD34 MoAb and PE-conjugated CD38 MoAb and analyzed by flow cytometry. Log fluorescence distribution of CD34 expression is shown along the X-axis and CD38 expression along the Y-axis. Each result is shown with its isotype control.

DESCRIPTION OF THE PREFERRED EMBODIMENTS

Bone marrow $CD34^+CD38^-$ cells are highly enriched for pluripotent progenitor cells which account for long term repopulation in vivo [31–33], but attempts at expanding $CD34^+CD38^-$ cells in-vitro for therapeutic use have had very limited success due to the differentiation and cell death which frequently occurs when these primitive cells are exposed to cytokines [3,6,34]. An ex-vivo co-culture system which has the capacity to expand the population of long term repopulating cells while maintaining their $CD34^+CD38^-$ phenotype would have immediate clinical applications in gene therapy, cord blood expansion, and stem cell transplantation protocols.

In this study, we demonstrate that primitive hematopoietic progenitor/stem cells actively proliferate and expand in direct association with preformed HUBEC monolayers, which is consistent with our previous observations using a porcine endothelial cell line [21]. Unlike liquid suspension cultures and non-CNS derived endothelial cell cultures, co-culture with HUJBEC is essential for expansion of the primitive $CD34^+CD38^-$ subset (440-fold at day 7) while maintaining their primitive phenotype and immature undifferentiated blast cell morphology. In addition, $CD34^+$ cell proliferation in HUBEC co-culture appears to be the greatest in the $CD34^+CD38^-$ cell population. While the addition of exogenous growth factors including GM-CSF, IL-3, IL-6, SCF and flt3-ligand are important for $CD34^+$ cell activation and expansion, additional as-yet unidentified endothelial cell factors most likely play a critical role in the $CD34^+CD38^-$ cell "self-renewal" processes [35]. In contrast, results from stroma-free and non-brain endothelial cell cultures demonstrate that cultured $CD34^+CD38^-$ fail to proliferate significantly, idifferentiate quickly, and overall CFC cell expansion.is limited and short lived. These results suggest that brain-derived endothelial cells provide a unique microenvironment which promotes the cell division and apparent self-renewal of the primitive $CD34^+CD38^-$ population.

We confirm that the majority of steady state bone marrow $CD34^+CD38^-$ cells are quiescent and reside primarily in $G_0$ of the cell cycle [22,36,37]. The lack of cell cycling induction within the most primitive $CD34^+CD38^-$ population has been identified as a major impediment to the successful transduction of these cells with retroviral based gene vectors [36,38]. We have previously determined that $CD34^+CD38^-$ cells are easily recruited into cell cycle when cultured on porcine brain endothelial cells (PMVEC) [22]. In the current study, we found that primary HUBEC cultures from numerous donors in combination with exogenous cytokines induced the majority (>70%) of the previously quiescent $CD34^+CD38^-$ population to enter $G_1$ or $G_2/S/M$ phase of cell cycle after 7 days. Although the mechanism of rapid expansion of $CD34^+CD38^-$ cells is unclear, HUBEC may provide the microenvironment necessary in combination with exogenous cytokines to induce rapid cycling and preserve the "stemness" of very primitive HPC (<2% of the total $CD34^+$ cells used to initiate cultures) and may also prevent apoptotic cell death. In contrast, we have found that this high level of cell division in $CD34^+CD38^-$ cells is not achievable in stroma-free liquid and human non-brain endothelial cocultures supplemented with GMCSF+IL-3+IL-6+SCF+flt-3 ligand. Unlike other stromal based culture systems [10,11], we do not observe inhibitory effects of endothelial cell contact on $CD34^+CD38$ expansion. In fact, in the HUBEC system, cell-to-cell contact promotes maximal expansion of the $CD34^+CD38^-$ cell population which is dependent upon the addition of a combination of exogenous growth factors and appears to override any type of direct endothelial cell inhibitory effects. These findings are consistent with our previously reported observations that $CD34^+CD38^-$ cell expansion is optimal when $CD34^+$ cells are cultured directly in contact with PMVEC monolayers rather than when cultured separately from the endothelial feeder cells using transwell inserts [21]. Since HUBEC provide a microenvironment which supports a high level of cell cycling and expands the primitive $CD34^+CD38^-$ population, this culture system may also promote higher efficiencies of gene transfer into transplantable cells using standard retroviral vectors.

Bone marrow $CD34^+CD38^-$ cells contain long term culture initiating cells (LTC-IC) which give rise to CFC over 6 weeks when cultured with stromal feeder layers [29,39]. Our clonogenic data in this study is consistent with that reported by others demonstrating that steady state $CD34^+CD38^-$ cells do not give rise to significant numbers of CFC when cultured directly in 14 day methylcellulose cultures plus cytokines [29,39]. For that reason, $CD34^+CD38^-$ cells typically have been characterized as having limited CFC activity. It has previously been reported that 10 day serum-free liquid cultures of human $CD34^+CD38^-$ cells with optimal cytokine combinations including flt-3 ligand, SCF, and IL-3 promoted a 30-fold increase in LTC-IC production by the expanded population [30]. Although the authors did not address the phenotype of the expanded population in that study, it is likely that the majority of the input $CD34^+CD38^-$ cells exposed to cytokines for 10 days underwent significant differentiation and lineage commitment. In contrast, we demonstrate in this study that co-culture of human $CD34^+CD38^-$ cells with preformed HUBEC monolayers plus cytokines supports rapid cycling and ex vivo expansion of phenotypically primitive HPC of the $CD34^+CD38^-$ subset. Since the HUBEC co-culture supports this pronounced increase in $CD34^+CD38^-$ cells, we were easily able to collect and study this rare subset of long term repopulating cells to interrogate their biology after 7 days of co-culture. Unlike $CD34^+CD38^-$ cells in the steady state, $CD34^+CD38^-$ cells expanded on HUBEC monolayers directly give rise to hundreds of colonies of myeloid, erythroid, and mixed, lineages in methylcellulose at a cloning efficiency of 24%. This suggests a period of pre-incubation in HUBEC co-culture plus cytokines can stimulate early HPC (stromal cell responsive progenitor cells) which would normally be cytokine unresponsive in a stroma-free microenvironment. In previous studies, we have shown that HSC expanded in PMVEC coculture are capable of competitive myeloid and lymphoid marrow repopulating when implanted into SCID-hu-bone and transplanted into lethally irradiated baboons [23,24]. Together these findings demonstrate the requirement for direct stem cell-stromal cell interaction in order to optimize HPC survival, expansion, and maintenance of HPC function under ex-vivo culture conditions and to preserve graft quality. Moreover, the ability to determine stroma cell dependent CFC frequencies in a short time interval makes the HUBEC culture system an attractive alternative to other long-term in vitro quantification methodologies. Likewise, the ability to activate and significantly expand $CD34^+CD38^-$ progenitor cell pool has potential ramifications in clinical stem cell expansion studies.

Recently, bone marrow microvascular and human umbilical vein endothelial lines have been used to support the short-term growth and proliferation of human $CD34^+$ progenitor cells [18,20]. However, the outcome of the primitive $CD34^+CD38^-$ subpopulation has not been detailed in these co-culture systems. More recently, a stromal cell line derived from murine fetal liver, AFT024, has been shown to support the maintenance of a small percentage of $CD34^+CD38^-$ cells over 3–10 days of co-culture [40]. The authors hypothesized in this study that the AFT024 cell line may have maintained extended long term culture initiating cells (ELTC-ICs) by inhibiting cell cycling and differentiation of these $CD34^+CD38^-$ cells [40]. In contrast to these observations, HUBEC co-culture induces a high level of cell cycling in the quiescent $CD34^+CD38^-$ subset and the absolute percentage of $CD34^+CD38^-$ cells is not only maintained, but increases~440-fold (0.3% at day 0 to 10.5%) at day 7. These data suggest that human brain endothelial cells may provide other hematopoietic signal(s) such as soluble growth factors, membrane-bound growth factors, extracellular matrix proteins, or cellular adhesion molecules, which are unique from fetal liver, bone marrow, or umbilical vein endothelial cell lines.

Since human brain endothelial cells support the apparent self renewal and expansion of primitive HPC whereas non-brain endothelial cells from the same donor do not, we speculate that the biology of brain endothelial cells may be similar to embryonic and extra-embryonicendothelial cells which are critically involved in the generation of hematopoietic stem cells during embryogenesis [14–16]. Recently, it was reported that a murine aorto-gonad-mesonephros (AGM) region derived endothelial cell line (DAS 104-4) was capable of maintaining a small fraction of murine $CD34^+$ Sca-1$^+$ c-kit$^+$ lin$^-$ cells over 7 days of co-culture and these hematopoietic cells retained their in vivo reconstituting capacity [41]. Based upon their findings, the authors hypothesized that the DAS 104-4 AGM-derived cell line was able to support the self renewal of a small percentage of hematopoietic stem cells [41]. Based upon their similar capacities to maintain primitive hematopoietic progenitor cells ex vivo, it is plausible that human brain endothelial cells may possess similar hematopoietic properties to AGM-derived endothelial cells. In addition, the profound induction of cell cycling and expansion of the $CD34^+CD38^-$ subpopulation observed on HUBEC monolayers suggests that brain endothelial cells may be providing novel hematopoietic signals as well.

In comparison to other ex-vivo cultures systems, we believe that the human brain endothelial cell (HUBEC) culture system has several major advantages which will prove useful in future clinical stem cell expansion and gene therapy studies. First, rapid amplification and collection of very large numbers cycling $CD34^+CD38^-$ cells can occur within 1 week of culture. Second, expansion of hematopoietic progenitor cells requires only preformed endothelial monolayers, which are easy to establish and maintain, plus a defined combination of commercially available cytokines. Third, we have shown that expansion of $CD34^+CD38^-$ cells requires only human brain endothelial cells (single cell type) whose hematopoietic biology should be more easily dissected compared to heterogeneous stromal cell systems. Fourth, we have previously shown that HPCs. expanded on porcine brain endothelial cell monolayers retain both in vivo myeloid and lymphoidrepopulating potential with no apparent engraftment defects [23,24]. Results from ongoing SCID-Hu and primate bone marrow transplantation studies utilizing primitive $CD34^+CD38^-$ cells expanded on HUBEC monolayers will be important in evaluating this system for future therapeutic applications.

Definitions

1. Human CD34+ hematopoietic stem cells (HSC): CD34+ cells isolated from various hematopoietic tissues (not limited to peripheral blood, bone marrow, cord blood, spleen, and liver) that are capable of full and permanent lymphoid, erythroid and myeloid reconstitution following transplantation into a lethally irradiated recipient. These cells are a subset of the CD34+CD38− HPC population.
2. HPC: Hematopoietic progenitor cells
3. CD34+CD38+ hematopoietic progenitor cells: Committed/differentiated CD34+ hematopoietic progenitor cells that express the lineage commitment surface marker CD38 and are functionally described as having only short-term hematopoietic reconstitution in vivo.
4. CD34+CD38− hematopoietic progenitor cells: The undifferentiated subset of CD34+ HPC cells that lacks CD38 expression and contains hematopoietic stem cells (HSC) which are functionally capable of long-term hematopoietic reconstitution. The HSC are located in the population of cells
5. SCF: Stem cell factor
6. IL-6: Interleukin-6
7. MGDF: Megakaryocyte growth and developmental factor
8. Long-term culture-initiating cells (LTC-IC): HSC that are defined by their potential to grow, proliferate and be maintained in stroma based cultures systems in the absence of exogenous cytokines over 5–7 weeks of culture.
9. Colony-forming cells (CFC): Committed progenitor cells (CD34+CD38+) that give rise to assayable in vitro colonies of either the myeloid, erythroid, or lymphoid lineages following 14 days of culture.
10. HUBEC: Human brain derived endothelial cells
11. GM-CSF: granulocyte macrophage colony-stimulating factor.
12. IL-3: Interleukin-3
13. MoAb: Monoclonal antibody
14. FACS: Fluorescent activated cell sorting
15. PE-CD38: Phycoerythrin conjugated anti-CD38 antibody
16. FITC-CD34: Fluorescein Isothiocyanate anti-CD34 antibody
17. SID: Surface intracellular DNA analysis
18. 7-AAD: 7-aminoactinomycin 19. FCS: Fetal bovine serum
20. CD34+Sca-1+c-kit+lin-cells: Primitive murine hematopoietic stem cells that have full and long-term hematopoietic reconstitution potential in vivo.
21. Flt3 (Rosnet et al. Oncogene, 6, 1641–1650, 1991) and flk-2 (Matthews et al., Cell, 65, 1143–1152, 1991) are variant forms of a TKR that is related to the c-fms and c-kit receptors. The flk-2 gene product is expressed on hematopoietic and progenitor cells, while the flt3 gene product has a more general tissue distribution. The flt3 and flk-2 receptor proteins are similar in amino acid sequence and vary at two amino acid residues in the extracellular domain and diverge in a 31 amino acid segment located near the C-termini (Lyman et al., Oncogene, 8, 815–822, 1993).
22. Flt3-ligand ("flt3-L") has been found to regulate the growth and differentiation of progenitor and stem cells and is likely to possess clinical utility in treating hematopoietic disorders, in particular, aplastic anemia and myelodysplastic syndromes. Additionally, flt3-L will be useful in allogeneic, syngeneic or autologous bone marrow transplants in patients undergoing cytoreductive therapies, as well as cell expansion. Flt3-L will also be useful in gene therapy and progenitor and stem cell mobilization systems.

EXAMPLES

Isolation and Culture of Prinmary Human Brain Endothelial Cells (HUBEC)

Short segments (<10 cm) of blood vessels contained within the central nervous system (segments of the anterior cerebral artery and vertebro-basilar artery branching from the Circle of Willis) and segments of vessels from outside the CNS (internal iliac artery and renal artery) were obtained from autopsy specimens less than 12 hours post-mortem after informed consent was obtained. Blood vessel segments were placed in 4° C. complete endothelial cell culture medium consisting of M199 (Gibco BRL, Grand Island, N.Y.) supplemented with 10% heat-inactivated FBS (Hyclone, Logan, Utah), 100 mcg/mL L-glutamine, 50 mcg/mL heparin, 30 mcg/mL endothelial cell growth factor supplement (Sigma, St. Louis, Mo.) and 100 mcg/mL penicillin/streptomycin solution.

Within 6 hours of primary dissection from the brain, blood vessels were gently washed twice with PBS (Ca2+; Mg2+ free) and transferred to gelatin-coated (need size) tissue culture dishes containing 2 mL of complete endothelial cell growth media. Using a sterile #10 scalpel blade, lmm cross sectional cuts were made along the length of the vessels. Larger vessels were first cut longitudinally with three incisions, to open and flatten the vessel, and then inverted to orient the vessel lumen towards the surface of the tissue culture dish. Immediately following the dissection an additional 2 mL of complete endothelial cell media was added to each dish. Cultures were placed in a humidified 37° C., 5% $CO_2$ atmosphere.

Distinct macroscopic cobblestone HUBEC colonies were evident between days 7–14 of culture. Following the establishment of confluent monolayers (~30 days), spent culture medium was collected and endothelial cell monolayers were washed vigorously with PBS (Ca++, Mg++Free), trypsinized (0.25 mg trypsin/mL, 5 mmol/L EDTA, 37° C., 10 minutes; GIBCO) and subcultured at a ratio of 1:5 into gelatin-coated 75 cm2 flasks (Costar, Cambridge, Mass.) containing 20 mL of complete endothelial cell culture medium. HUBEC monolayers were fed weekly with complete medium and several passages of the primary cells were established and banked.

Characteristics of Human Brain Endothielial Cells

Figure 1B:
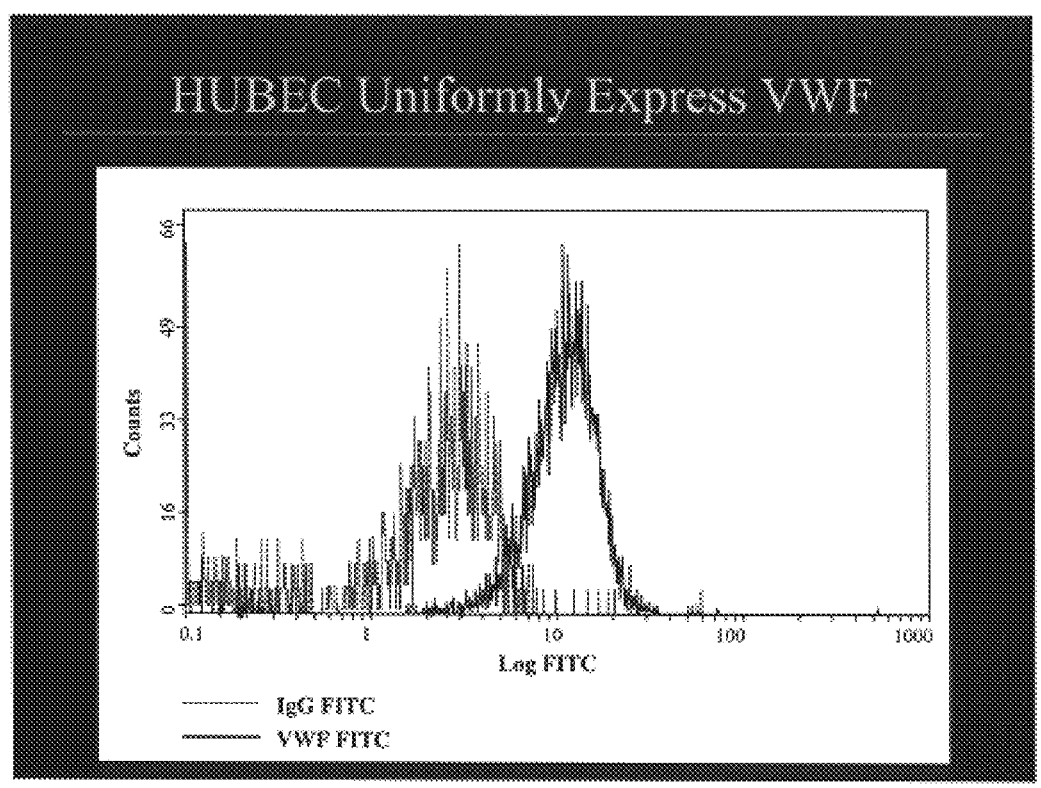

HUBEC from passages, 1–10 appeared morphologically identical with no observable differences in the rate of growth noted. Cultures developed the typical uniform endothelial cell monolayer cobblestone morphology when 80–100% confluent (FIG. 1A). Cells at passages 5–10 were harvested using 5 mM EDTA and stained with a monoclonal antibody against human Von Willebrand Factor, and then analyzed by flow cytometry. As shown in FIG. 1B, Von Willebrand Factor is highly expressed on HUBEC. HUBEC do not express either the CD34 or CD38 antigen at significant levels (<5%, data not shown).

Expansion of Bone Marrow CD34+ Cells on HUBEC Monolayers

Figure 2A:
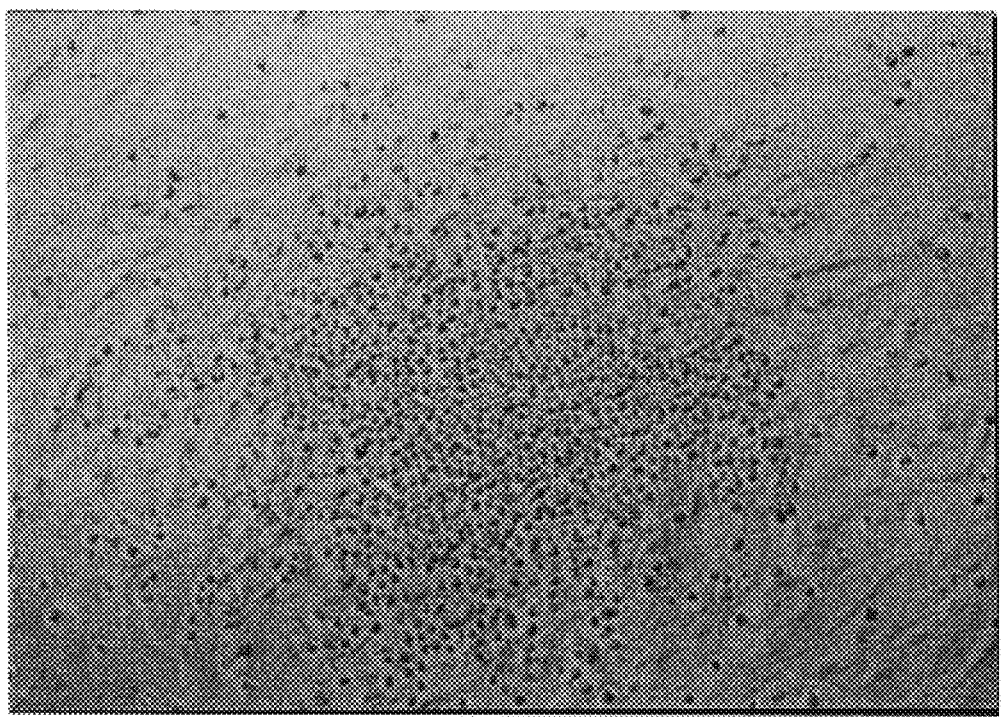
FIGS. 2A and 2B. Morphology of a typical adherent colony of hematopoietic cells following 7 days of co-culture of human bone marrow CD34+ cells on HUBEC monolayers treated with Granulocyte monocyte colony stimulating factor (GMCSF)+ Interleukin-3 (IL-3)+Interleukin-6 (IL- 6)+ Stem cell factor (SCF)+ fetal liver tyrosine kinase-3 ligand (flt-3 ligand).
Figure 2B:
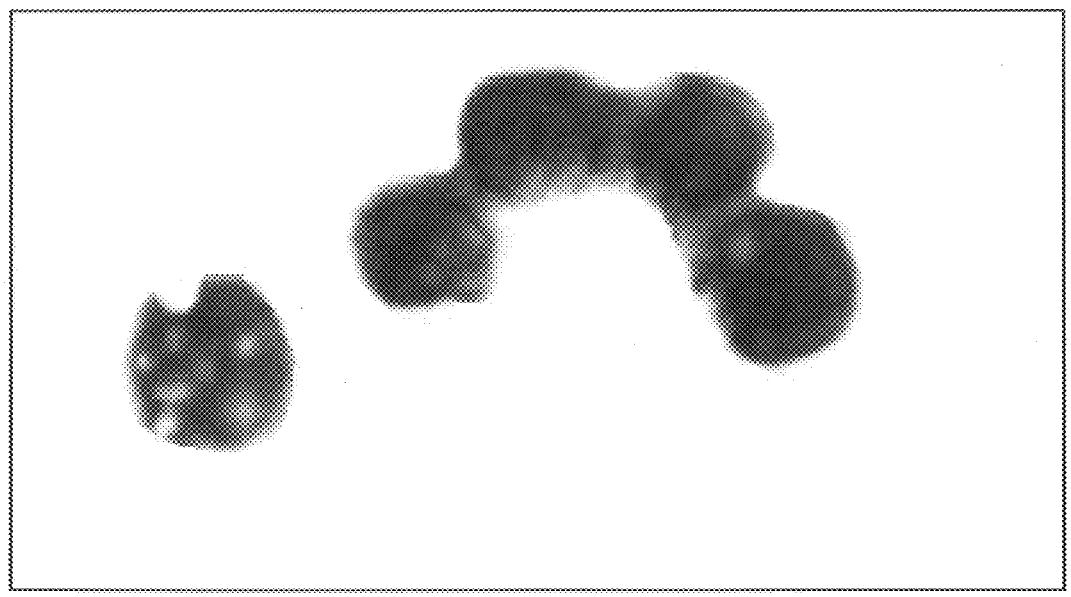
Figures 1A, 3:
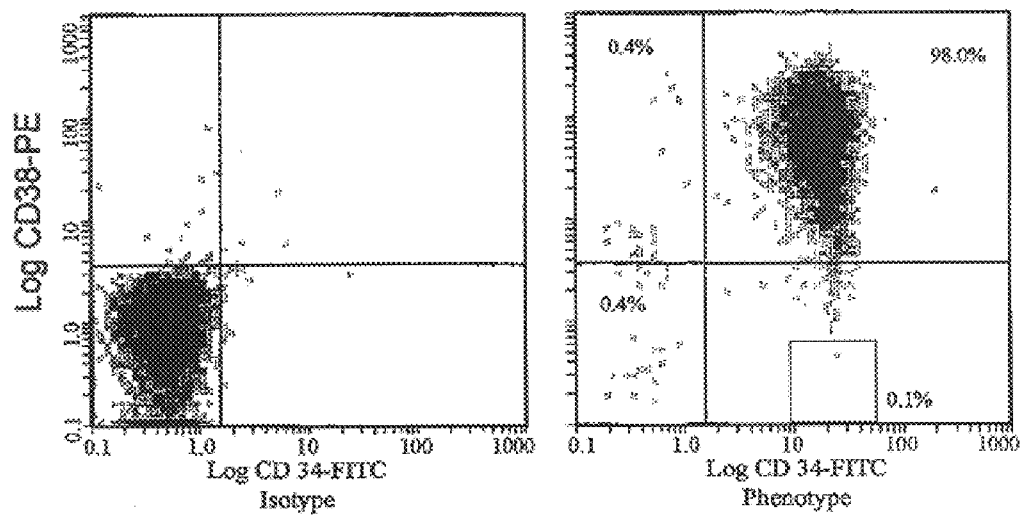
Figures 1B, 3:
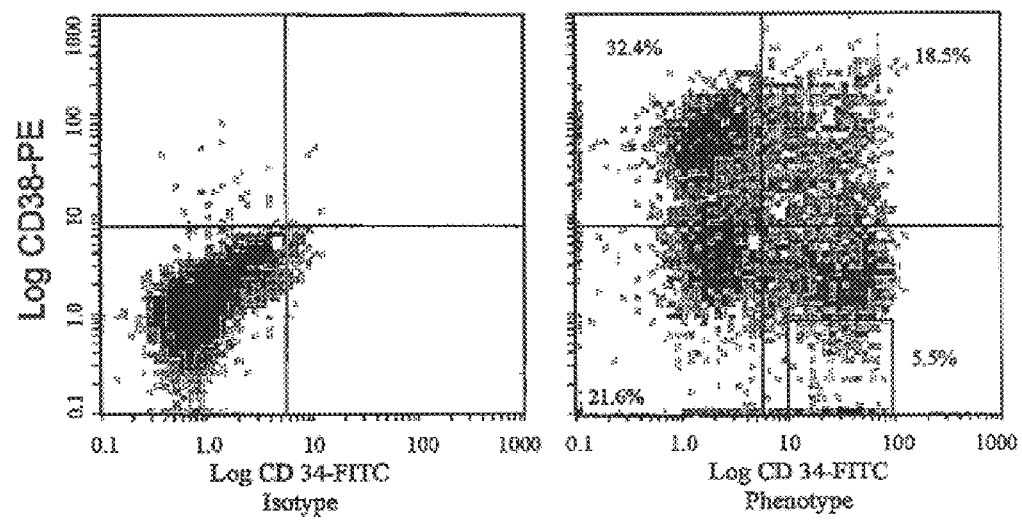
Figures 2C, 3:
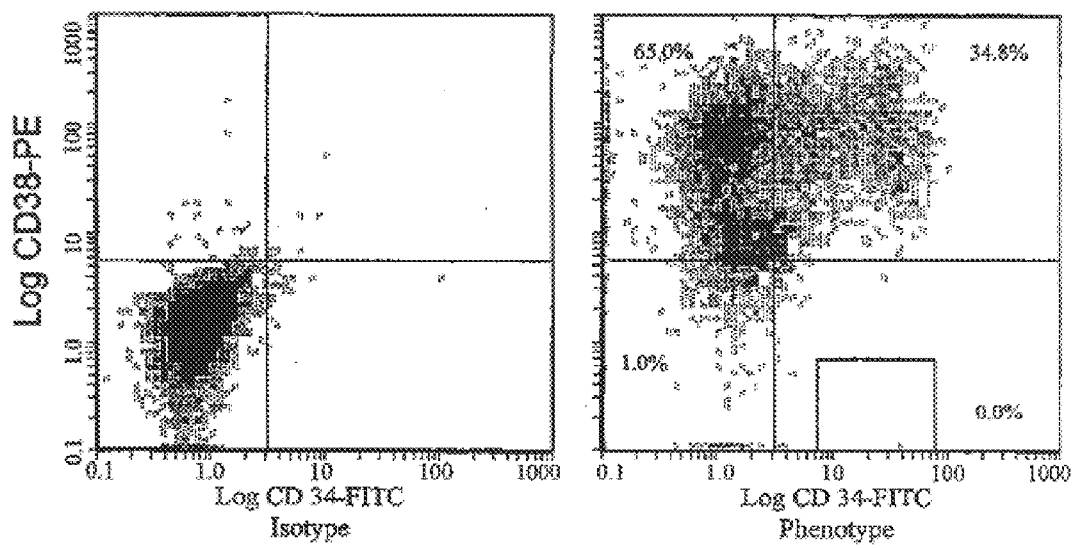
Figures 2D, 3:
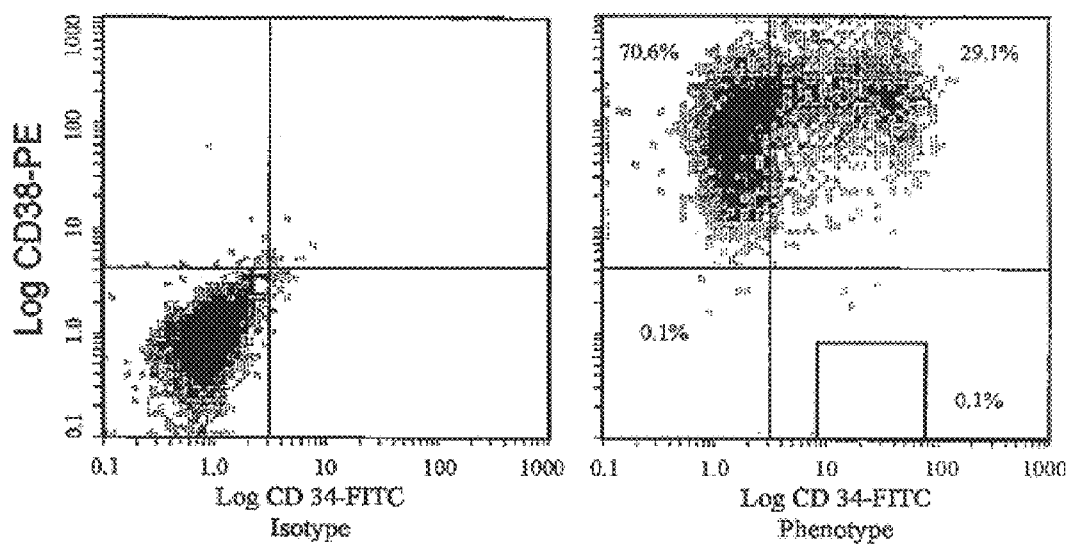

Human $CD34^+$ cells were isolated from normal human cadaveric bone marrow as previously described [21] with >96% purity. The effects of HUBEC co-culture on $CD34^+$ cell proliferation and CFC generation were initially compared with stroma-free liquid suspension cultures and co-cultures utilizing. human non-brain endothelial cells isolated from the same cadaveric donors. All cultures were treated identically with a combination of five stimulatory cytokines (GM-CSF+IL-3+IL-6+SCF+flt-3 ligand) previously shown to support optimal $CD34^+$ cell proliferation [21]. After 7 days of co-culture, large macroscopic colonies (>2000 cells) developed on HUBEC in which the majority of the cells could be dispersed and collected by gently washing of the HUBEC monolayers with culture medium. Remaining cells (<11%) appeared to be tightly adherent and embedded within the HUBEC monolayer resembling "cobblestone-like hematopoietic foci" (FIGS. 2A & 2B). In the absence of exogenously supplied growth factors very little cell growth was observed. At day 7 of HUBEC coculture, the mean number of total nonadherent and $CD34^+$ cells increased 13.4- and 6.4-fold, respectively, with a 453-fold increase in the number of $CD34^+CD38^-$ cells (Table 1). Forty-eight percent of the harvested nonadherent cells following 7 days of HUBEC coculture expressed the CD34 antigen. The $CD34^+CD38^-$ subpopulation, defined as $CD34^+$ cells that expressed CD38PE fluorescence at least one half less than the PE-isotype control, increased from a mean of 0.3% of the population at day 0 to 10.5% of the total nonadherent cell population at day 7 and constituted 21% of the day 7 expanded $CD34^+$ cell pool (Table 1). FIGS. 3-1A and 3-1B show a representative phenotype of bone marrow $CD34^+$ cells at day 0 (3A) and after 7 days of HUBEC co-culture (3B). $CD34^+CD38^-$ cells isolated by cell sorting from day 7 HUBEC co-cultures are primarily agranular blasts with a high nuclear to cytoplasmic ratio, a fine chromatin pattern, and prominent nucleoli.

We also compared the capacity of the HUBEC coculture system to expand $CD34^+CD38^-$ cells and multilineage CFC with stroma-free liquid suspension cultures and with non-brain endothelial cell cocultures using the identical combination of exogenous cytokines over 7–14 days of culture. Maximal nonadherent (233-fold) and total $CD34^+$ cell expansion (21-fold) was detected following 14 days of culture using the HUBEC coculture system (Table 2), with a 1690-fold increase in the absolute number of $CD34^+$ CD38⁻ cells. Additionally, CFU-GM, CFU-Mix and BFU-E CFC progenitors increased 558-, 129-, and 180-fold respectively (Table 3). In comparison, overall cell and CFC yields were significantly lower in stroma-free liquid suspension and in non-brain endothelial cell co-cultures (Tables 2 and 3). Total $CD34^+$ cell numbers were maintained or moderately increased ($\leq$7-fold) over 14 days under these culture conditions with little or no amplification of the $CD34^+$ $CD38^-$ cell population detected following 7 days of ex vivo culture. Representative day 7 phenotypes of hematopoietic cells expanded in liquid suspension cultures and non-brain endothelial cell cocultures are shown in FIGS. 3C and 3D.

TABLE 1

Ex-vivo Expansion of Human Bone Marrow $CD34^+$ and $CD34^+CD38^-$ Cells in Cytokine-Treated HUBEC Cultures

| | | No. of Cells Procured × $10^5$ | | |
|---|---|---|---|---|
| Culture Conditions | Cell yield × $10^5$ | $CD34^+$ | $CD34^+CD38^+$ | $CD34^+CD38^-$ |
| Input $CD34^+$ Cells | 5.0 | 5.0 (100) | 4.85 (97) | 0.015 (0.3) |
| HUBEC Co-culture (day 7) | 67 ± 17.1 | 32 ± 7.0 (100) | 25.3 ± 7.4 (79) | 6.8 ± 3.9 (21) |

$CD34^+$ BM cells (5 × $10^5$) were plated per culture treatment. Nonadherent cells were procured on day 7 of culture. Cells of each culture were stained for phenotypic analysis with FITC-conjugated CD34 (HPCA-2) plus PE-conjugated CD38). Stained cells were analyzed using two-color flow cytometry. The number of each immunophenotype was corrected to reflect the total number of cells procured/culture. Each point represents the mean number of positive cells from five different experiments. Numbers in parentheses indicate the relative frequency of a given phenotype calculated as a percentage of total $CD34^+$ cells.

TABLE 2

In Vitro Expansion of $CD34^+$ Cell Subsets in HUBEC Coculture versus Stroma-free and Non-brain Endothelial Cell Cocultures

| | | No. of Cells Procured × $10^5$ | | |
|---|---|---|---|---|
| Culture Conditions | Cell yield × $10^5$ | $CD34^+$ | $CD34^+CD38^+$ | $CD34^+CD38^-$ |
| Input | 5.0 | 5.0 | 4.99 + 0.01 | 0.01 + 0.01 |
| HUBEC Co-culture | | | | |
| Day 7 | 72.3 ± 2.6 | 33.0 ± 1.0 | 28.9 ± 0.9 | 4.4 ± 0.2 |
| Day 14 | 1163.0 ± 43.6 | 104.3 ± 57.0 | 87.3 ± 5.0 | 16.9 ± 1.0 |
| Stroma-free | | | | |
| Day 7 | 51.0 ± 1.3 | 15.1 ± 0.7 | 15.1 ± 0.6 | 0.02 ± 0.02 |
| Day 14 | 396.0 ± 80.0 | 35.0 ± 2.8 | 35.0 ± 2.8 | 0 |
| Non-CNS EC Co-culture | | | | |
| Day 7 | 52.0 ± 2.8 | 18.1 ± 12.6 | 18.1 ± 12.6 | 0 |
| Day 14 | nd | nd | nd | nd |

$CD34^+$ BM cells (5 × $10^5$) were plated per culture treatment. Non-adherent cells were procured on day 7 and 14 of culture. Cells of each culture were stained for phenotypic analysis with FITC-conjugated CD34 (HPCA-2) plus PE-conjugated CD38). Stained cells were analyzed using two-color flow cytometry. The number of each immunophenotype was corrected to reflect the total number of cells procured/culture. Each point represents the mean number of positive cells from two different experiments. nd: no data

TABLE 3

Effects of HUBEC Co-culture on Hematopoietic Progenitor Cell Production in Comparison to Stroma-free and Human Non-brain Endothelial Cell Co-cultures.

| | Number of CFC × $10^4$ | | | |
|---|---|---|---|---|
| Culture Conditions | CFU-GM | CFU-Mix | BFU-E | Total CFC |
| Input | 3.7 + 0.9 | 0.5 + 0.2 | 0.6 + 0.3 | 4.7 + 1.4 |
| HUBEC Co-culture | | | | |
| Day 7 | 56.0 ± 2.2 | 2.6 ± 0.3 | 4.8 ± 0.6 | 63.4 ± 2.5 |
| Day 14 | 2065.0 ± 49.0 | 64.5 ± 2.5 | 108.0 ± 9.5 | 2240.0 ± 70.7 |
| Stroma-free | | | | |
| Day 7 | 15.8 ± 4.5 | 0.5 ± 0.9 | 0.7 ± 0.7 | 17.1 ± 4.6 |
| Day 14 | 200.0 ± 42.4 | 3.6 ± 0.2 | 19.8 ± 2.6 | 228.0 ± 41.0 |

TABLE 3-continued

Effects of HUBEC Co-culture on Hematopoietic Progenitor Cell Production in
Comparison to Stroma-free and Human Non-brain Endothelial Cell Co-cultures.

| Culture Conditions | Number of CFC × 10$^4$ | | | |
|---|---|---|---|---|
| | CFU-GM | CFU-Mix | BFU-E | Total CFC |
| Non-CNS EC Co-culture | | | | |
| Day 7 | 22.2 ± 4.9 | 0.6 ± 0.3 | 4.8 ± 0.3 | 27.7 ± 6.2 |
| Day 14 | nd | nd | nd | nd |

5 × 10$^5$ CD34$^+$ bone marrow cells were plated per culture treatment. Nonadherent cells were harvested on day 7 of culture. Nonadherent cells (5–500 × 10$^2$) were cultured in 35-mm tissue culture dishes containing IMDM medium, 1% methylcellulose, 30% FCS, optimal concentrations of EPO, GM-CSF, IL-3 and SCF. The number of myeloid and erythroid colonies were counted after 14 days of culture, and based on the total number of viable cells per culture the number of colonies was corrected to reflect the total number of CFC per culture condition. Values represent the number of colonies of triplicate cultures from two different experiments. nd: no data.

Cell Cycle Analysis

In another series of experiments, we studied the role of HUBEC co-culture on the cell cycle status of ex-vivo expanded CD34$^+$ cells. Analysis of CD34$^+$CD38$^-$ cells at day 0 demonstrated that 92.9% of the cells were in $G_0$, 5.9% were in $G_1$, and 1.2% were in $G_2$/S/M phase. After 7 days of HUBEC co-culture, 55.2% of the CD34$^+$CD38$^-$ cells had entered $G_1$, 38.7% were in $G_2$/S/M phase, and only 5.8% remained in $G_0$. Similar analysis of the CD34$^+$CD38$^+$ subset indicated that 29.8%, 52.5%, and 17.2% of the CD38$^+$ cells were in $G_0$, $G_1$, and $G_2$/S/M phase at day 7, respectively. Analysis of CD34$^+$ cells from stroma-free and non-CNS endothelial cell cultures was not performed due to the relatively low/undetectable frequency of CD34$^+$CD38$^-$ cells following 7 days of culture.

Effect of ex vivo HUBEC Co-culture on the Clonogenic Capacity of CD34$^+$CD38$^-$ Cells in Methylcellulose CFC Cultures To determine whether 7 days of HUBEC co-culture could enhance the in vitro clonogenic capacity of CD34$^+$CD)38$^-$ cells, we FACS sorted and collected CD34$^+$, CD34$^+$CD38$^-$, and CD34$^+$CD38$^+$ cell populations prior to and following 7 days of HUBEC co-culture. CD34$^+$CD38$^-$ and CD34$^+$CD38$^+$ cells could be easily collected in all samples analyzed. Sort windows were established to give a clear separation of CD34$^+$CD38$^-$ and CD34$^+$CD38$^{bright}$ cells, and therefore most of the CD34$^+$CD38$^{dim}$ cells were excluded from the analysis. Five hundred cells from each cell population were seeded into 1% methylcellulose containing Iscove's modified Dulbecco's medium (IMDM), supplemented with optimal concentrations of EPO, GM-CSF, IL-3, IL-6, and SCF and scored for total CFC formation after 14 days of incubation. As shown in Table 4 and consistent with previous studies [29,30], very few, if any, steady state CD34$^+$CD38$^-$ cells (0.035%) were able to form colonies in standard methylcellulose based clonogenic media. Colonies derived from CD34$^+$CD38$^-$ cells were smaller on average than colonies derived from steady state CD34$^+$CD38$^+$ cells (cloning efficiency 11.9%) cultured under identical culture conditions. As expected, the CD34$^+$CD38$^+$ subset demonstrated a cloning efficiency which approximated the cloning efficiency of the entire steady state CD34$^+$ population (consisting of ~98% CD34$^+$CD38$^+$ cells), thereby confirming that the large majority of colonies generated from steady state CD34$^+$ cells arise from the CD34$^+$CD38$^+$ subset with little or no contribution from the CD34$^+$CD38$^-$ subset.

In contrast to the results obtained culturing steady state CD34$^+$CD38$^-$ progenitor cells, when activated/expanded CD34$^+$CD38$^-$ cells were stringently re-selected from HUBEC monolayers after 7 day of coculture, a 685-fold expansion (from 0.035% cloning efficiency at day 0 to 24.0% cloning efficiency at day 7) of CFC was detected. The number of assayable CFC was greater in cultures initiated with CD34$^+$CD38$^-$ cells (24.0% cloning efficiency) than in cultures initiated with CD34$^+$CD38$^{bright}$ cells (16.8%), but lower when compared to unsorted CD34$^+$ cells (40.1%). This is most likely due to the fact that CD34$^+$CD38$^{dim}$ cells which have a high clonogenic potential comprise a significant portion of the day 7 CD34$^+$ cell pool and these were excluded from our analysis in the setting of stringent sort windows. In addition to increased colony numbers, an increase in colony size was also observed for cultures initiated with expanded and sorted CD34$^+$CD38$^-$ in comparison to CD34$^+$CD38$^+$ cells. Evaluation of the sorted CD34$^-$ cells from HUBEC co-cultures showed that this population was practically devoid of CFC (0.3%). These plating efficiencies indicate that the majority of CFC generated following 7 days of HUBEC co-culture arises from the CD34$^+$CD38$^-$ and CD34$^+$CD38$^{dim}$ populations with significantly less contribution from the CD34$^+$CD38$^{bright}$ subset.

TABLE 4

Frequency of CFC in Sorted CD34$^+$ Cell Populations

| Cell Population | CFC Frequency (%) | | |
|---|---|---|---|
| | Experiment 1 | Experiment 2 | Mean |
| Input CD34$^+$ Cells (d-0) | | | |
| Unsorted CD34$^+$ | 13.4 ± 4.1 | 12.8 ± 3.7 | 13.1 |
| CD34$^+$CD38$^-$ | 0.07 ± 0.01 | 0 | 0.035 |
| CD34$^+$CD38$^+$ | 11.4 ± 3.5 | 12.4 ± 4.3 | 11.9 |
| HUBEC Co-culture (d-7) | | | |
| Unsorted nonadherent cells | 19.9 ± 1.1 | 19.9 ± 1.9 | 19.9 |
| CD34$^+$ | 42.2 ± 2.6 | 37.9 ± 1.2 | 40.1 |
| CD34$^+$CD38$^-$ | 28.9 ± 5.3 | 19.1 ± 2.8 | 24.0 |
| CD34$^+$CD38$^+$ | 17.1 ± 4.6 | 16.4 ± 1.7 | 16.8 |
| CD34$^-$ | 0.2 ± 0.2 | 0.4 ± 0.1 | 0.3 |

TABLE 4-continued

Frequency of CFC in Sorted CD34+ Cell Populations

| | CFC Frequency (%) | | |
|---|---|---|---|
| Cell Population | Experiment 1 | Experiment 2 | Mean |

At day 0 and after 7 days of HUBEC co-culture CD34+, CD34+CD38+, CD34+CD38−, and CD34− cell populations were collected by FACS sorting cells labeled with FITC-conjugated anti-human CD34 mAb and PE-conjugated anti-human CD38 mAb. Cells were cultured at 500 cells/dish in 1% methylcellulose containing Iscove's modified Dulbecco's medium (IMDM), supplemented with optimal concentrations of EPO, GM-CSF, IL-3, and SCF. The cultures were assessed at day 14 for colony-forming cells (CFC). Based on the total number of viable cells per culture the number of colonies was corrected to reflect the total number of CFC per culture condition. Values represent the number of colonies of triplicate cultures from two different experiments.

REFERENCES

1. Haylock D N, To L B, Dowse T L, Juttner C A, Simmons P J (1992) Ex vivo expansion and maturation of peripheral blood CD34+ cells into the myeloid lineage. Blood 80:140
2. Brugger W, Mocklin W, Heimfeld S, Berenson R J, Mertelsmann R, Kanz L,(1993) Ex vivo expansion of enriched peripheral blood CD34+ progenitor cells by stem cell factor, interleukin- 1B, IL-6, IL-3, interferon-gamma, and erythropoietin. Blood 81: 2579
3. Srour E G, Brandt J E, Briddell R A, Grigsby S, Leemhuis T, Hoffinan R (1993) Long term generation and expansion of human primitive hematopoietic progenitor cells in vitro. Blood 81:661
4. Nolta J A, Smorgorzewska E M, Kohn D B (1995) Analysis of optimal conditions for retroviral-mediate transduction of primitive human hematopoietic cells. Blood 86: 101
5. Bodine D M, Crosier P S, Clark S C (1991) Effects of hematopoietic growth factor on the survival of primitive stem cells in liquid suspension culture. Blood 78: 914
6. Emerson S G (1996) Ex vivo expansion of hematopoietic precursors, progenitors, an stem cells: the next generation of cellular therapeutics. Blood 87: 3082
7: Auiti A, Friedrich C, Sieff C A, Gutierrez-Ramos J C (1998) Identification of distinct elements of the stromal microenviroinment that control human hematopoietic stem/progenitor cell growth and differentiation. Exp Hematol 26: 143
8. Dexter T M, Alleng D, Lajtha L G (1977) Conditions controlling the proliferation of haemopoietic stem cells in vitro. J Cell Physiol 91: 335
9. Dorshkind K (1990) Regulation of hemopoiesis by bone marrow stromal cells and their products. Annu Rev Immunol 8: 11
10. Verfaille C M (1992) Direct contact between human primitive hematopoietic progenitors and bone marrow stroma is not required for long term in vitro hematopoiesis. Blood 79: 2821
11. Verfaille C M (1993) Soluble factor(s) produced by human bone marrow stroma increase cytokine-induced proliferation and maturation of primitive hematopoietic progenitors while preventing their terminal differentiation. Blood 82: 2045
12. Verfaille C M, Catanzarro P M, Li W (1994) Macrophage inflammatory protein 1α, interleukin 3, andtdiffusible marrow stromal factors maintain human hematopoietic stem cells for at least eight weeks in vitro. J Exp Med 179: 643
13. Piacibello W, Sanavio F, Severino A, Dane A, Gammaitoni L, Fagioli F, Perissinotto E, Cavalloni G, Kollet O, Lapidot T, Aglietta M (1999) Engraftment in nonobese diabetic severe combined immunodeficient mice of human CD34+ cord blood cells after ex vivo expansion: evidence for the amplification and self-renewal of repopulating stem cells. Blood 93: 3736
14. Shalaby F, Rossant J, Yamaguchi T P, Gertsenstein M, Wu X, Breitman M L, Schuh A C (1 995) Failure of blood-island formation and vasculogenesis in flk-1 deficient mice. Nature 376:62
15. Eichmann A, Corbel C, Nataf V, Vaigot P, Breant C, Le Douarin N M (1997) Ligand-dependent development of the endothelial and hemopoietic lineages from embryonic mesodermal cells expressing vascular endothelial growth factor receptor 2. Proc Natl Acad Sci USA 13:5141
16. Choi K, Kennedy M, Kazarov A, Papadimitriou J C, Keller G (1998) A common precursor for hematoppietic and endothelial cells. Development 125: 725
17. Raffi S, Shapiro F, Rimarachin J, Nachman R L, Ferris B, Weksler B, Moore M A S, Asch A S (1994) Isolation and characterization of human bone marrow microvascular endothelial cells: hematopoietic progenitor cell adhesion. Blood 84: 10
18. Raffi S, Shapiro F, Pettengell R, Ferris B, Nachman R L, Moore M A S, Asch A S (1995) Human bone marrow microvascular endothelial cells support long term proliferatin anddifferentiation of myeloid and megakaryocytic progenitors. Blood 86: 3353
19. Lu L S, Wang S J, Auerbach R (1996) In vitro and in vivo differentiation into B cells, T cells, and myeloid cells of primitive yolk sac hematopoietic precursor cells expanded >100 fold by coculture with a clonal yolk sacendothelial cell line. Proc Natl Acad Sci 93: 14782
20. Yamaguchi H, Ishii E, Saito S, Tashiko K, Fujita I, Yoshidomi S, Ohtubo M, Akazawa K, Miyazaki S (1996) Umbilical vein endothelial cells are an important source of c-kit and stem cell factor which regulate the proliferation of haematopoietic progenitor cells. Br J Haematol 94: 606
21. Davis T A, Robinson D H, Lee K P, Kessler S W (1995) Porcine brain microvascular endothelial cells support the in vitro expansion of human primitive hematopoietic bonemarrow progenitor cells with ahighreplating potential: requirement for cell-to-cell interactions and colony-stimulating factors. Blood 85: 1751
22. Chute J P, Saini A A, Karnpen R L, Wells M R, Davis T A (1999) A comparative study of the cell cycle status and primitive cell adhesion molecule profile of human CD34+ cells cultured in stroma-free versus porcine microvascular endothelial cell cultures. Exp Hematol 27: 370
23. Brandt J E, Galy A H, Luens K M, Travis M, Young J, Tong J, Chen S, Davis T A, Lee K P, Chen B P, Tushinski R, Hoffman R (1998) Bone marrow repopulation by human marrow stem cells after long term expansion culture on a porcine endothelial cell line. Exp Hematol 26: 950
24. Brandt J E, Bartholomew A, Fortman J D, Nelson M C, Bruno E, Chen L M, Turian J V, Davis T A, Chute J P, Hoffinan R (1999) Ex vivo expansion of autologous bone marrow stem cells with porcine microvascular endothelial cells results in a graft capable of rescuing lethally irradiated baboons. Blood 94: 106
25. Spatz M, Kawai N, Merkel N, Bembry J, McCarron R M (1997) Functional properties of cultured endothelial cells derived from large microvessels of human brain. Am J Physiol 272: C231–239
26. Stins M F, Gilles F, Kim K S (1997) Selective expression of adhesion molecules on human brain microvascular endothelial cells. J Neuroimmunol 76: 81–90

27. Lou J, Dayer J M, Grau G E, Burger D (1996) Direct cell/cell contact with stimulated T lymphocytes induces the expression of cell adhesion molecules and cytokines by human brain microvascular endothelial cells. Eur J Immunol 26: 3107
28. Jordan C T, Yamasaki G, Minamoto D (1996) High resolution cell cycle analysis of defined phenotypic subsets within primitive human hematopoietic cell populations. Exp Hematol 24: 1347
29. Petzer A L, Hogge D E, Landsdorp R M, Reid D S, Eaves C J (1996) Self renewal of primitive human hematopoietic cells (long term culture initiating cells) in vitro and their expansion in defined medium. Proc Natl Acad Sci USA 93: 1470
30. Petzer A L, Zandstra P W, Piret J M, Eaves C J (1996) Differential cytokine effects on primitive (CD34+CD38−) human hematopoietic cells: Novel responses to flt3-ligand and thrombopoietin. J Exp Med 183: 2551
31. Huang S, Terstappen W M M (1994) Lymphoid and myeloid differentiation of single human CD34+, HLA-DR+, CD38− hematopoietic stem cells. Blood 83:1515
32. Terstappen L W, Huang S, Safford M, Lansdorp P, Loken M (1991) Sequential generations of hematopoietic colonies derived from single nonlineage committed CD34+ CD38− progenitor cells. Blood 77:1218
33. Bhatia M, Wang J C, Kapp U. Bonnet D, Dick J E (1997) Purification of primitive humanhematopoietic cells capable of repopulating immune-deficient mice. Proc Natl Acad Sci USA 94: 5320
34. Lansdorp P M, Dragowska W, Mayani H (1993) Ontogeny-related changes in proliferative potential of human hematopoietic cells. J Exp Med 178:787
35. Davis T A, Davis T A, Black A T, Kidwell W R, Lee K P (1997) Conditioned medium from primary porcine endothelial cells alone promotes the growth of primitive human hematopoietic progenitor cells with a high replating potential: evidence for a novel early haematopoietic activity. Cytokine 9:263
36. Agrawal Y P, Agrawal R S, Sinclair A M, Young D, Maruyama M, Levine F, HO A D (1996) Cell cycle kinetics and VSV-G pseudotyped retrovirus mediated gene transfer in blood-derived CD34+ cells. Exp Hematol 24: 738
37. Hao Q L, Shah A J, Thiemann F T, Smogorzewska E M, Crooks G M (1995) A functional comparison of CD34+ CD38− cells in cord blood and bone marrow. Blood 86: 3745
38. Miller D G, Adam M A, Miller A D (1990) Gene transfer by retrovirus vectors occurs only in cells that are actively replicating at the time of infection. Mol Cell Biol 10:
39. Sutherland H J, Eaves C J, Lansdorp P M, Thacker J D, Hogge D E (1991) Differential regulation of primitive human hematopoietic cells in long-term cultures maintained on genetically engineered munine stromal cells. Blood 78: 666
40. Thiemann F T, Moore K A, Smogorzewska E M, Lemischka I R, Crooks G M (1998) The murine stromal cell line AFT024 acts specifically on human CD34+ CD38− progenitors to maintain primitive function and immunophenotype in vitro. Exp Hematol 26: 612
41. Ohneda O, Fennie C, Zheng Z, Donahue C, La H, Villacorta R, Cairns B, Lasky L A (1998) Hematopoietic stem cell maintenance and differentiation are supported by embryonic aorta-gonad-mesonephros region-derived endothelium. Blood 92: 908.

Obviously, many variations and combinations of the invention can be seen from the above specificexamples. The above examples are intended to disclose the best mode currently known to the inventors and is not intended to limit the invention.

What is claimed is:

1. A method of expanding human bone marrow CD34+ CD38− hematopoietic progenitor cells, including primitive stem cells, in vitro, comprising the steps of:
   i) isolating and culturing human brain endothelial cells by dissecting segments of blood vessels from the Circle of Willis;
   ii) contacting isolated CD34+CD38− hematopoietic progenitor cells with the isolated and cultured human brain endothelial cells; and
   iii) co-culturing the contacted CD34+CD38− hematopoietic progenitor cells and endothehal cells in the presence of at least one cytokine in an amount sufficient to support amplification/expansion of said CD34+CD38− hemratopoietic progenitor cells.

2. A method of expanding human bone marrow CD34+ CD38− hematopoietic progenitor cells, including primitive stem cells, in vitro, comprising the steps of:
   i) isolating and culturing human brain endothelial cells by dissecting segments of blood vessels from the Circle of Willis;
   ii) isolating CD34+CD38− hematopoietic progenitor cells from human bone marrow;
   iii) contacting the isolated CD34+CD38− hematopoietic progenitor cells with the isolated and cultured human brain endothelial cells; and
   iv) co-culturing the contacted CD34+CD38− hematopoietic progenitor cells and endothelial cells in the presence of at least one cytokine in an amount sufficient to support aniplification/expanston ofCD34+CD38− hematopoietic progenitor cells.

3. The method according to claim 1 or 2, wherein said CD34+CD38− hematopoietic progenitor cells are contacted with a semi-confluent monolayer of the endothelial cells.

4. The method according to claim 1 or 2, wherein said cytokine is selected from the group consisting of a mixture of granulocyte-macrophage colony stimulating factor and stem cell factor; a mixture of interleukin-3, stem cell factor, and interleukin-6; a mixture of granulocyte-macrophage colony stimulating factor, interleukin-3, stem cell factor, and interleukin-6.

5. The method according to claim 1 or 2, wherein said cytokine is granulocyte-macrophage colony stimulating factor.

6. The method according to claim 4, wherein said cytokine is a mixture of granulocyte-macrophage colony stimulating factor, interleukin-3, stem cell factor arid interleukin-6.

7. A method of amnplifgin/expanding human CD34+ CD38− hematopoietic progenitor cells, in vitro, which comprises the steps of:
   i) isolating and culturing human brain endothelial cells by dissecting segments ofbood vessels from the Circle of Willis;
   ii) contacting isolated CD34+CD38− hematopoictic progenitor cells with the isolated and cultured human brain endothelial cells; and
   iii) co-culturing the contacted CD34+CD38− hematopoietic progenitor cells and endothelial cells in the presence of a mixture of granulocyte-macrophage colony stimulating factor, interleukin-3, stem cell factor and interleukin-6 in an amount sufficient to amplify/expand said CD34+CD38− bematopoietic progenitor cells.

8. The method of claim 1 or 7, wherein the step i) further comprises a step of cutting the vessels longtitudinally.

9. The method of claim 1 or 7, wherein the step i) further comprises a step of cutting the vessels so the lumen of each vessel is exposed.

10. The method of claim 9, wherein the step i) further comprises a step of orienting each vessel lumen towards the surface of a tissue culture dish.

11. A method of amphifying/expanding human CD34+ CD38− hematopoietic progenitor cells, in vitro, which comprises the steps of:
   i) isolating and culturing human brain endothelial cells by dissecting segments of blood vessels from the Circle of Willis;
   ii) isolating the CD34+CD38− hematopoietic progenitor cells from humnan bone marrow;
   iii) contacting the isolated CD34+CD38− hematopoietic progenitor cells with the isolated and cultured humnan brain endothelial cells; and
   iv) co-culturg the contacted CD34+CD38− hematopoietic progenitor cells and endothelial cells in the presence of a mixture of granulocyte-macrophage colony stimulating factor, interlekukin-3, stem cell factor and interleukin-6 in an amount sufficient to amplify/expand said CD34+CD38− hematopoictic progenitor cells.

12. A growth medium for in vitro cell expansion comprising human brain endothelial cells isolated by dissecting segments of blood vessels from the Circle of Willis and a cytokine selected from the group consisting of granulocyte-macrophage colony stimulating factor, interleukin-3, stem cell factor, interleukin-6, tyrosine kinase-3 ligand and combinations thereof.

13. The growth medium of claim 12, said medium comprising a monolayer of human brain endothelial cells.

14. A method of isolating and culturing human brain endothelial cells, said method comprising the step of isolating and culturing human brain endothelial cells by dissecting segments of blood vessels from the Circle of Willis.

15. The method of claim 14, further comprising the step of orienting the vessel lumen towards the surface of a tissue culture dish.

* * * * *